United States Patent [19]

Sufrin et al.

[11] Patent Number: 5,180,714

[45] Date of Patent: Jan. 19, 1993

[54] ADENOSINE COMPOUNDS FOR THE TREATMENT OF DISEASES CAUSED BY PARASITIC PROTOZOA

[75] Inventors: Janice R. Sufrin, Snyder; Cyrus J. Bacchi, E. Northport; Carl W. Porter, East Aurora; Henry Nathan, Riverdale; Arthur J. Spiess, Cheektowaga; Nigel Yarlett, Elmhurst, all of N.Y.

[73] Assignee: Health Research, Inc., Buffalo, N.Y.

[21] Appl. No.: 606,587

[22] Filed: Oct. 31, 1990

[51] Int. Cl.$^5$ .............................................. A61K 31/70
[52] U.S. Cl. ...................................... 514/46; 536/26; 536/27.6; 514/45; 514/23
[58] Field of Search ........................ 536/26; 514/45, 46

[56] References Cited

U.S. PATENT DOCUMENTS

| | | | |
|---|---|---|---|
| 3,212,954 | 10/1965 | Kuhn et al. | 167/65 |
| 4,242,505 | 12/1980 | Kawahara et al. | 536/26 |
| 4,373,097 | 2/1983 | Stramentinoli et al. | 536/26 |
| 4,376,116 | 3/1983 | Coward et al. | 424/180 |
| 4,454,122 | 6/1984 | Stramentinoli et al. | 424/180 |
| 4,558,122 | 12/1985 | Gennari | 536/26 |
| 4,621,056 | 11/1986 | Gennari | 435/85 |
| 4,820,692 | 4/1989 | Riscoe et al. | 536/1.1 |
| 4,914,086 | 4/1990 | Bacchi et al. | 514/45 |

OTHER PUBLICATIONS

D. L. Kramer et al., "Biological Effects of a Novel Fluorinated Analog of 5'-Dioxy-5'-(methylthio) adenosine (MTA)", Abstract-American Association for Cancer Research, May 25-28, 1988, published as volume 29, Mar. 1988.

J. R. Sufrin, "Synthesis and Antiproliferative Effects of Novel 5'-Fluorinated Analogues of 5'-Deoxy-5'-(methylthio) adenosine", Journal of Medicinal Chemistry, 1989 vol. 32, No. 5.

M. J. Robins et al., "Fluorination at C5' of Nucleosides, Synthesis of the New Class of 5'-Fluoro-5'-S-Aryl (Alkyl) Thionucleosides from Adenosine", Tetrahedron Letters, vol. 29, No. 45, pp. 5729-5732 (1988).

K. Kikugawa et al., "Platelet Aggregation Inhibitors, 2 Inhibition of Platelet Aggregation by 5'-,2-,6-, and 8-Substituted Adenosines[1]", Journal of Medicinal Chemistry, 1972, vol. 15, No. 4, pp. 387-391.

J. Hildesheim et al., "Studies on Synthetic Inhibitors of t-RNA Methyl Transferases: Analogs of S-adenosyl Homocysteine", Biochimie, 1973, 55, 514-546.

P. Chiang et al., "S-Adenosyl-L-homocysteine Hydrolase: Analogues of S-Adenosyl-L-homocysteine as Potential Inhibitors", Molecular Pharmacology, 13, 939-947, 1977.

J. Enouf et al., "Relationship Between Inhibition of Protein Methylase I and Inhibition of Rous Sarcoma Virus-induced Cell Transformation", Cancer Research 39, 4497-4502, Nov. 1979.

C. S. Marvel et al., "The Structure of Propylene Polysulfone", Journal of American Chemical Society, vol. 76, pp. 61-69 (1954).

J. A. Montgomery, "Analogs of 5'-Deoxy-5'-(methylthio) adenosine", Journal of Medicinal Chemistry, 1974, vol. 17, No. 11, pp. 1197-1203.

M. K. Riscoe et al., "Methionine Recycling as a Target for Antiprotozoal Drug Development", Parasitology Today, vol. 5, No. 10, pp. 330-333 (1989).

L. Y. Ghoda et al., "Substrate Specificities of 5'-deoxy-5'-methylthioadenosine phosphorylase from Trypanosoma brucei brucei and Mammalian Cells", Molecular and Biochemical Parasitology, 27, pp. 109-118 (1988).

M. K. Riscoe et al., "Analogs of 5-Methylthiribose, and Novel Class of Antiprotozoal Agents", Antimicrobial Agents and Chemotherapy, Dec. 1988, pp. 1904-1906.

G. W. Koszalka et al., "5'-Methylthioadenosine (MTA) Phosphorylase from Promastigotes of Leishmania Donovani", Purine and Pyrimidine Metabolism in Man V, Edited by W. L. Nyhan et al., Plenum Publishing Corporation, 1986.

R. L. Miller et al., "Trypanosoma Cruzi Adenine Nucleoside Phosphorylase", Biochemical Pharmacology, vol. 36, No. 00, pp. 553-559 (1987).

A. J. Bitonti et al., "Cure of Trypanosoma brucei brucei and Trypanosoma brucei rhodesiense Infections in Mice with an Irreversible Inhibitor of S-Adenosylmethionine Decarboxylase, Antimicrobial Agents and Chemother." 34, 1485, 1990.

A. J. Bitonti et al., "Bis(benzyl)polyamine Analogs Inhibit the Growth of Chloroquine-Resistant Human Malaria Parasites (Plasmodium falciparum) in vitro and in Combination with a difluoromethylornithine Cure Murine Malaria", Proc. Natl. Acad. Sci., vol. 86, pp. 651-655, Jan. 1989.

(List continued on next page.)

Primary Examiner—John W. Rollins
Assistant Examiner—L. Eric Crane
Attorney, Agent, or Firm—James F. Mudd; Michael L. Dunn

[57] ABSTRACT

The compounds 5'-deoxy-5'-(hydroxyethylthio)adenosine (HETA); 5'-deoxy-5'-(monofluorethylthio)adenosine (MFETA); 5'-deoxy-5'-(chloroethylthio)adenosine (CETA); 5'-deoxy-5'-(bromoethylthtio)adenosine (BETA); 5-deoxy-5-(monofluoroethylthio)ribose (MFETR); 5-deoxy-5-(chloroethylthio)ribose (CETR); 5-deoxy-5-(bromoethylthio)ribose (BETR) and 5-deoxy-5-(hydroxyethylthio)ribose (HETR), are described as well as their uses in treating infections caused by 5'-deoxy-5'-methylthioadenosine (MTA) phosphorylase-containing pathogenic microorganisms; in treating infections caused by 5-deoxy-5-methylthioribose (MTR) kinase-containing pathogenic microorganism; and for treating neoplastic diseases.

9 Claims, No Drawings

OTHER PUBLICATIONS

K. F. Baum et al., "Purine Deoxynucleoside Salvage in Giardia Lamblia", J. Biol. Chem. 264, 21087, 1989.

H. G. Williams-Ashman et al., "Trends in the Biochemical Pharmacology of 5-Deoxy-5'-methylthioadenosine", Giochem. Pharmacol. 31, 277, 1982.

T. M. Savarese et al., "Biochemical Considerations in the Design of Analogs of 5'-Deoxy-5'methylthioadenosine, in *Development of Target-Oriented Anticancer Drugs*", Y. C. Chang, ed., Raven Press, N.Y., pp. 129-142 (1983).

R. Tritapepe et al., "5'-Methylthioadenosine (MTA) for the Topical Treattment of Angiological Disorders", Acta Therapeutics 15, 299, 1989.

J. I. Toohey et al., "Methylthioadenosine Nucleoside Phosphorylase Deficiency in Methylthio-Dependent Cancer Cells", Biochem. Biophys. Res. Commun. 83, 27, 1978.

J. H. Fitchen et al., "Methylthioadenosine Phosphorylase Deficiency in Human Leukemias and Solid Tumors", Cancer Res. 46, 5409, 1986.

S. T. Traweek et al., "Methylthioadenosine Phosphorylase Deficiency in Acute Leukemia: Pathologic, Cytogenetic and Clinical Features", Blood. 71, 1568, 1989.

R. M. Hoffman, "Altered Methionine Metabolism and Transmethylation in Cancer", Anticancer Res. 5, 1, 1985.

T. M. Savarese et al., "Conversion of 5'-Deoxy-5'methylthioadenosine and 5'-Deoxy-5'-Deoxy-5'-methylthioinosine to Methionine in Cultured Human Leukemic Cells", Cancer Res. 43, 4699, 1983.

C. J. Bacchi et al., "Parasitic Protozoa and Polyamines, in *Inhibition of Polyamine Metabolism*", P. P. McCann, A. E. Pegg and A. Sjoerdsma, Eds. Academic Press, Inc., Orlando, Fla., pp. 317-344.

R. M. Myers et al., "Conversion of 5-S-Ethyl-5-thio-D-ribose to Ethionine in *Klebsiella Pneumoniae*", J. Biol. Chem. 264, 10547, 1989.

*Hanessian et al.*, Carbohydrate Research 24, 45 (1972).

"Synthesis of Antiprolyerative Effects of 5'-fluoronated analogs of 5'-deoxy-5'-(methylthio)adenosin", Sufria et al. CA110(21) 193314b (1989).

"Prep of 5'-deoxy-5'-fluoroethylthionbonucleosides and antiluation agents containing them", Yoshiro et al. CA 110(7):58012m.

"Effect of adenosylhoniscystein and other analog tioethers" Paslella et al. CA 97 (25): 211354j (1982).

"Comparative Biochemistry and Drug Design for Infectious Disease", Cohen, Science vol. 205, Sep. 7, 1979.

ADENOSINE COMPOUNDS FOR THE TREATMENT OF DISEASES CAUSED BY PARASITIC PROTOZOA

This invention was made under research grant 5U01-CA 37606 awarded by the National Cancer Institute of the National Institutes of Health of the U.S. Department of Health and Human Services, and research grant AI 17340 awarded by National Institutes of Health of the U.S. Department of Health and Human Services.

BACKGROUND OF THE INVENTION

This invention relates to agents for the treatment of diseases caused by parasitic protozoa. More particularly, the invention relates to agents for the treatment of *Trypanosoma brucei brucei* infections. *T. b. brucei* is the type organism of a group which cause African human and veterinary trypanosomiasis. These organisms include *T. b. brucei*, *Trypanosoma brucei rhodesiense* and *Trypanosoma brucei gambiense*. The invention further relates to compounds found to be active against a strain of *Trichomonas vaginalis*, and against *Plasmodium falciparum*, a causative agent of malaria, indicating a broader spectrum of antiprotozoal effects for the compounds of the invention.

The invention further relates to compounds for the treatment of malignant or neoplastic diseases.

Trypanosomiasis, or sleeping sickness, is a disease of widespread proportions which is endemic to Africa. One of the more promising developments in recent years, relating to the treatment of this disease as well as of malaria, has been the discovery that inhibitors of polyamine biosynthesis such as α-difluoromethylornithine (DFMO), E-2-fluoromethyldehydroornithine methyl ester, bis-benzyl polyamine analogs and most recently, MDL73811, an irreversible inhibitor of S-adenosylmethionine decarboxylase are highly effective agents for their treatment, as disclosed in the following literature:

C. J. Bacchi et al., Parasitic Protozoa and Polyamines, in *Inhibition of Polyamine Metabolism*, P. P. McCann, A. E. Pegg and A. Sjoerdsma, editors, Academic Press, Inc., Orlando, Fla. pp 317-344.

A. J. Bitonti et al. Bis(benzyl)polyamine Analogs Inhibit the Growth of Chloroquine-resistant Human Malaria Parasites in vitro and in Combination with α-Difluoromethylornithine Cure Murine Malaria. Proc. Natl. Acad. Sci., USA 86, 651 (1989) and A. J. Bitonti et al. Cure of *Trypanosoma brucei brucei* and *Trypanosoma brucei rhodesiense* Infections in Mice with an Irreversible Inhibitor of S-Adenosylmethionine Decarboxylase. Antimicrob. Agents Chemother. 34, 1485, 1990.

U.S. Pat. No. 4,914,086 discloses certain compounds that are useful in treating trypanosomiasis. While the compounds have the structure of nucleosides, their trypanocidal activity does not suggest the use of analogs of 5'-deoxy-5'-methylthioadenosine (MTA) because the biochemical activity is not related to polyamine metabolism. The disclosure of this patent is hereby incorporated by reference.

A further development in the field is disclosed in U.S. Pat. No. 4,820,692 which focuses on a group of thioribose compounds, but also discloses certain corresponding nucleosides. The ribose compounds are said to be analogs of 5-deoxy-5-methylthioribose (MTR) which have a variety of substituents R at the 5-position which can be H, Cl, F, Br, I or $R_1S$- in which $R_1$ is $C_1$-$C_{10}$ linear or branched chain alkyl or halogenated $C_1C_{10}$ linear or branched chain alkyl. The preparation of the compounds where R is halogen or $R_1$ is alkyl is disclosed. The thioribose compounds are disclosed to be useful as medicinal and biocidal agents in a selected number of pathogenic microorganisms, which have been shown to contain the enzyme 5-methylthioribose kinase (MTR kinase). Applicants have discovered a select few compounds disclosed in this patent that are unexpectedly useful in the treatment of diseases caused by 5'-deoxy-5'-methylthioadenosine (MTA) phosphorylase-containing microorganisms. This is in contrast to structurally similar compounds that are not useful in the treatment of such diseases. The preparation of Applicants' compounds is not disclosed in the patent. The use of compounds for the treatment of malignancies is not disclosed in the patent.

The compound 5'-deoxy-5'-(methylthio)adenosine (MTA), has well documented growth inhibitory activity although the exact mechanism of its growth inhibition remains obscure. Numerous analogs of MTA have been synthesized and investigated for their growth inhibitory and chemotherapeutic effects, such as disclosed by Montgomery et al., J. Med. Chem. 17, 1197, 1974, and Savarese et al. in Development of Target-Oriented Anticancer Drugs Y. C. Chang, ed., Raven Press, New York 1983, pp 129-142. The types of structural modifications which have been incorporated into MTA analogs include: 1) carbon for nitrogen replacements in the purine ring; 2) addition of exo-cyclic substituents on the purine ring, and 3) replacement of the 5'-methyl substituent of the ribose ring with numerous other alkyl or aryl substituents. As structurally modified analogs of a growth inhibitory cellular metabolite, the chemotherapeutic potential of these compounds has been explored. Of particular interest is a recent clinical study which has shown the promise of MTA, itself, as an agent for the treatment of topical disorders—most notably, venous ulcers, as disclosed by Tritapepe et al. in Acta Therapeutica 15, 299, 1989.

One aspect of the cellular biochemistry of MTA relates to the enzyme MTA phosphorylase. This enzyme catalyzes the degradation of MTA to adenine and 5-methylthioribose-1-phosphate (MTR-1-P). The degradation of MTA by MTA phosphorylase keeps cellular concentrations of MTA extremely low, thereby protecting the cell from the growth inhibitory effects of MTA. In 1978, Toohey first noted in Biochem. Biophys. Res. Commun. 87, 27, 1978, that some murine leukemia cell lines are devoid of MTA phosphorylase activity. Subsequently, clinical studies reported by Fitchen et al. at Cancer Res. 46, 5409, 1986, have found that MTA phosphorylase deficiency is found in a small but significant number of solid tumors and leukemias, with the greatest incidence among patients with acute lymphocytic leukemia of T cell origin as disclosed by Traweek et al. in Blood, 71, 1568, 1989. Since MTA phosphorylase has been detected in all non-neoplastic mammalian cells that have been examined, chemotherapeutic strategies which exploit this tumor specific deficiency in MTA phosphorylase, may be possible.

Savarese et al. have suggested that MTA analog substrates of MTA phosphorylase might be selectively cytotoxic, based on their ability to produce growth inhibitory metabolites of adenine and/or MTR-1-P which would interfere with the recycling of purines and/or of methionine. Among such cell types are those which have been designated as "methionine dependent" tumor cells by Hoffman in Anticancer Res. 5, 1, 1985. Methionine dependence is thus an additional tumor specific defect in methionine metabolism which can occur independent of, or in association with MTA phosphorylase deficiency.

It is a purpose of this invention to synthesize substrate analogs of MTA which would be activated by MTA phosphorylase to produce analogs of MTR-1-P which would interfere with methionine recycling, a process which could be selectively growth inhibitory in methionine dependent tumor cells or in other pathogenic microorganisms.

SUMMARY OF THE INVENTION

It has now been found that the following nucleoside compounds are unexpectedly useful in the treatment of diseases, caused by certain parasitic protozoa, preferably 5'-deoxy-5'-methylthioadenosine (MTA) phosphorylase—containing microorganisms.

5'-deoxy-5'-(hydroxyethylthio)adenosine (HETA)
5'-deoxy-5'-(monofluoroethylthio)adenosine (MFETA)
5'-deoxy-5'-(chloroethylthio)adenosine (CETA)
5'-deoxy-5'-(bromoethylthio)adenosine (BETA)

The preferred nucleoside for treatment of parasitic protozoa is HETA, based on performance, stability and toxicity.

The above-listed compounds have also been found useful for the chemotherapeutic treatment of malignant or neoplastic diseases.

The preferred nucleoside for the treatment of tumors is MFETA, based on performance.

Other compounds of interest are the following thioribose compounds:

5-deoxy-5-(hydroxyethylthio)ribose (HETR)
5-deoxy-5-(monofluoroethylthio)ribose (MFETR)
5-deoxy-5-(chloroethylthio)ribose (CETR)
5-deoxy-5-(bromoethylthio)ribose (BETR)

DETAILED DESCRIPTION OF THE INVENTION

The compounds HETA, CETA, BETA and MFETA have been found surprisingly to be highly active against several 5'-deoxy-5'-methylthioadenosine (MTA) phosphorylase containing pathogenic microorganisms which include the following:

*Trypanosoma brucei brucei* (*T. b. brucei*)
*Plasmodium falciparum* (*P. falciparum*)
*Trypanosoma brucei rhodesiense* (*T. b. rhodesiense*)
*Trypanosoma brucei gambiense* (*T. b. gambiense*)

Other pathogenic microorganisms known to contain MTA phosphorylase include:

*Trypanosoma cruzi*
*Leishmania donovani*
*Leishmania tropica*
*Leishmania brasiliensis*

Another pathogenic microorganism that appears to contain MTA phosphorylase includes:

*Trichomonas vaginalis*

HETA has proven highly effective as an antitrypanosomal agent in mice infected with *T. b. brucei* and has shown these therapeutic effects in a wide dose range. As an analog of MTA, HETA is a member of a new class of polyamine pathway inhibitors to show significant antitrypanosomal activity. Its apparently low host toxicity makes it of interest as a potential antiparasitic agent. Also noteworthy is its straightforward two step synthesis from an inexpensive starting material, making HETA an easily and economically obtained therapeutic agent. Whereas Kikugawa et al. prepared HETA in 51% yield, we have modified the general synthetic procedure which they refer to for preparation of HETA, and have significantly improved the yield ($\geq 71\%$) of this compound.

In addition to its significant activity against agents of African trypanosomiasis, HETA was highly effective in a standard growth assay against *T. vaginalis* (laboratory strain C1-NIH), the cause of the sexually transmitted disease, trichomoniasis, which infects a large proportion of the U.S. population. Furthermore, CETA was found to be active against a Flagyl-resistant strain ATCC 50143 (CDC-85). The present and only antitrichomonal drug, Flagyl (1-ethoxy-5-nitro-imidazole) has several disadvantages. Because of potential mutagenic properties, the drug is not available to women during the first trimester of pregnancy. In addition, there is an increasing incidence of resistance, currently estimated at 10%; this amounts to a significant number of patients due to the prevalence of the disease. The absence of alternative treatment for this category of patients clearly indicates the need for alternative safer drugs to treat the disease.

*P. falciparum*, the causative agent of cerebral malaria, is the target of an intensive search for alternative drugs stemming largely from growing resistance to classical agents such as chloroquin and quinine. The patentees of U.S. Pat. No. 4,820,692 have found *P. falciparum* to contain MTR kinase and to be sensitive to the effects of the thioribose analog, 5-ethylthioribose (ETR). In contrast, we have found the growth of the microorganism is also inhibited by HETA or ETA but not by HETR in an in vitro screen, an indication that MTA phosphorylase is also present in this microorganism.

In accordance with this invention, it has been found that the nucleoside analogs MFETA and HETA are converted to the trypanocidal 5-deoxy-5-methylthioribose-1-phosphate (MTR-1-P) analogs, 5-deoxy-5-(monofluoroethylthio)ribose-1-phosphate (MFETR-1-P) and 5-deoxy-5-(hydroxyethylthio)ribose-1-phosphate (HETR-1-P), respectively, in *T. b. brucei*, which is an MTA-phosphorylase containing microorganism. Based on the respective abilities of 5-deoxy-5-(monofluoroethylthio)ribose (MFETR) and 5-deoxy-5-(hydroxyethylthio)ribose (HETR) to be converted, respectively to the identical, potentially toxic products, MFETR-1-P and HETR-1-P, in MTR kinase-containing organisms, the compounds HETR and MFETR would be the preferred effective agents for treating infections caused by MTR kinase-containing microorganisms.

The thioribose compounds of the invention, HETR, MFETR, CETR and BETR, may have utility as biocides against microorganisms which contain MTR kinase and which therefore have the ability to phosphorylate the thioribose.

Alternatively, the respective phosphates of the thioriboses may likewise be effective as biocides against microorganisms which lack MTR kinase and which therefore do not have the ability to phosphorylate the thioribose.

Pathogenic microorganisms known to contain MTR kinase include:

*Giardia lamblia*
*Candida albicans*
*Staphyloccus aureus*

Throughout this specification and claims, all temperatures are given in degrees Celsius and weights are given in grams, unless specified otherwise.

I. Preparation of the Compounds

The compound HETA can be produced in accordance with Kikugawa et al. in "Platelet Aggregation Inhibitors. 2. Inhibition of Platelet Aggregation by 5'-,2-,6-, and 8-Substituted Adenosines. J. Med. Chem. 15, 387, 1972. Certain improvements were made which improved the yield from about 50 percent to about 70 percent. Following is a description of the preferred method for producing HETA.

EXAMPLE A

Preparation of
5'-deoxy-5'-(hydroxyethylthio)adenosine (HETA)

Mercaptoethanol (8.83 ml) was added to a solution of NaOH (5.19 g) in water (27 ml). After stirring 0.5 hr, this mixture was added to a flask containing 5'-deoxy-5'-chloroadenosine (10 g) and the reaction mixture heated to 80 C on a hot plate with stirring for 2 hours. The flask was removed from the hot plate and allowed to stand at room temperature overnight or longer (3 days). A solidified precipitate remained in the flask, and water was added to facilitate its dissolution into a filterable precipitate. The product was filtered and washed with water. It was then recrystallized from water and the resulting, purified product, filtered and dried. Methanol was added to form a slurry which was then evaporated under vacuum to give 9.4 g HETA (81.8%); mp 190°-192° C. (softens at 120° C.). Elemental analysis was correct for HETA.

When the general procedure of Kikugawa et al. was used, the reaction mixture was heated for one hour. Under these conditions, workup yielded a product which also contained unreacted starting material and which was then retreated with mercaptoethanol solution. Kikugawa's procedure was thus modified so that the reaction mixture was heated for two hours, thereby insuring completeness of reaction. The Kikugawa et al. procedure was modified by omitting the acidification step with acetic acid.

EXAMPLE B

Preparation of 5'-Deoxy-5'-(chloroethylthio)adenosine (CETA)

Thionyl chloride (3.7 ml, 4.3 g, 36.2 mM) was added to 31 ml hexamethylphosphoramide (HMPA) at 0° with stirring, under nitrogen. After 30 minutes, HETA (4.0 g, 12.2 mM) in solid form, was introduced slowly to prevent clumping and stirring was continued an additional 2-4 hr at 0° C. until thin layer chromatography (TLC) ($CH_2Cl_2$/MeOH; 21:4) indicated disappearance of starting material. The contents of the reaction flask were then poured onto an ice-water mixture (200 ml), to form a gummy residue, the pH was adjusted to 9 with ammonium hydroxide and the aqueous mixture was extracted 3 times with 200 ml portions of $CH_2Cl_2$. The combined organic extracts were dried over $MgSO_4$, filtered and evaporated to give an oil (1.9 g), which upon purification by silica gel column chromatography yielded 450 mg (11%) of CETA as a white solid. Elemental analysis was correct for the compound ($C_{12}H_{16}N_5O_3ClS$).

EXAMPLE C

Preparation of 5'-Deoxy-5'-(bromoethylthio)adenosine (BETA)

Thionyl bromide (1.4 ml, 3.8 g, 18.3 mM) was added to 9.5 ml HMPA cooled at 0.C under argon. The solution was allowed to come to room temperature over 30 minutes and HETA (4.0 g, 12.2 mM) was added in portions as a dry solid. TLC ($CH_2Cl_2$/MeOH; 21:4) showed the reaction to be complete by the end of 3 hr at which time a 400 ml mixture of ice and water was added. The reaction mixture was stirred until complete dissolution was achieved, and the pH was adjusted within the range of 9-10 at 0° C. The cold aqueous mixture was extracted 3 times with 150 ml portions of ethyl acetate. The combined organic extracts were dried over $MgSO_4$, filtered and evaporated in vacuo to give a semisolid residue. Co-evaporation with $CH_2Cl_2$ gave a white solid residue which was purified on a silica gel column. 200 mg (4.2%) of BETA was obtained as a white solid. Elemental analysis was correct for the compound ($C_{12}H_{10}N_5O_3SBr$).

EXAMPLE D

Preparation of
5'-Deoxy-5'-(monofluoroethylthio)adenosine (MFETA)

(1) A solution of mercaptoethanol (21.7 ml, 24.2 g, 309 mM) and sodium hydroxide (12.65 g, 316 mM) in 72 ml water was stirred with cooling for 30 minutes. The solution was then transferred to a 500 ml beaker and 5'-deoxy-5'-chloro-2',3'-isopropylideneadenosine (42 g, 129 mM) was added with stirring. The resultant mixture was slowly heated to 105°-108° C. and its volume increased to approximately 200 ml by addition of water. Heating and stirring were continued an additional 1.5-2 hours at which time TLC (silica gel, $CH_2Cl_2$/MeOH:22/3) indicated disappearance of starting material and volume was decreased by one half. The reaction mixture was cooled in an ice bath, the aqueous layer decanted, and the highly viscous organic layer dissolved in approximately 200 ml $CH_2Cl_2$. This was washed with 3×75 ml $H_2O$, dried over $MgSO_4$ and filtered. The filtrate was stored below 0° C. for several days, allowing the product to crystallize. Recrystallization from $CH_2Cl_2$/MeOH/petroleum ether yielded a first crop of 18.4 g and upon further cooling of the mother liquor, a second crop of 4.9 g. Total recovered yield of 5'-deoxy-5'-(hydroxyethylthio)-2',3'-isopropylideneadenosine was 22.5 g (47.5%) mp 136°-137° C. Elemental analysis was correct for the compound ($C_{15}H_{21}N_5O_4S$).

(2) A dried 500 ml round bottom flask containing product from (1) (10.0 g 27.2 mM) and a magnetic stirring bar, was charged with argon and capped with a rubber septum. Dry $CH_2Cl_2$ (250 ml) was injected and the flask then cooled with stirring in a dry ice/ethanol bath for 20 minutes. To this was slowly injected diethylaminosulfur trifluoride (DAST) (10.8 ml, 13.2 g, 81.7 mM). After 40 minutes the flask was transferred to an ice/water bath and after 1½-2 hours, when TLC ($CH_2Cl_2$/MeOH: 22:3) indicated disappearance of starting material, the reaction mixture was poured into 350 ml of ice cold saturated aqueous sodium bicarbonate. After extraction with 3×300 ml $CH_2Cl_2$, the combined organic layers were dried over $MgSO_4$, filtered and evaporated in vacuo to give a 2.2 g of a residual foam.

This was applied to a Florisil column in CH₂Cl₂ and chromatographed with 500 ml CH₂Cl₂ and then CH₂Cl₂ containing 1% MeOH. In this manner, 1.28 g (12.7%) of 5'-deoxy-5'-(monofluoroethylthio)-2',3'-isopropylideneadenosine was obtained as a white solid. Recrystallization from EtOAc/Et₂O/hexane, gave an analytically pure sample of product (2): mp 113°-114° C. Elemental analysis was correct for the compound ($C_{15}H_{20}N_5O_3SF$).

(3) 5'Deoxy-5'-(monofluoroethylthio)-2',3'-isopropylideneadenosine (2.4 g, 3.5 mM) was dissolved in 43 ml 70% formic acid and stirred overnight at room temperature. Solvent was then removed in vacuo to give an oily residue which was repeatedly coevaporated with water and then methanol, to remove traces of formic acid. The residue was then dissolved in a minimum amount of methanol and purified on a silica column to give the compound MFETA (1.26 g, 59%) as a white solid. Elemental analysis was correct for the compound ($C_{13}H_{18}N_5O_3SF \cdot 2/3\ CH_3OH$).

EXAMPLE E

Preparation of 5-Deoxy-5-(hydroxyethylthio)ribose (HETR)

1. Methyl 5-deoxy-5-chloro-2,3-O-isopropylidene-ribofuranoside (MCIR) was prepared from methyl 2,3-isopropylidene ribfuranoside according to Hanessian et al. (Carbohydrate Res. 24, 45, 1972).

2. A solution of NaOH (40 g), mercaptoethanol (11.34 ml) and water (37.5 ml) was stirred at 0° C. for 0.5 hr and then added to a round bottom flask containing MCIR (15.0 g). The reaction mixture was heated with stirring at 80° C. for 3 days and then cooled. The reaction mixture was extracted with ether (3×100 ml) and the combined ether extracts washed with saturated aqueous NaCl. The ether extract was decolorized with Norit, filtered, dried with MgSO₄, filtered and concentrated under vacuum. The residue was chromatographed on a silica gel column to give methyl 5-deoxy-5-hydroxyethylthio-2,3-isopropylidene-ribofuranoside (MHETIR) (10 g).

3. MHETIR (2.0 g) was refluxed in 25 ml 0.1 N sulfuric acid for 1.5 hr, cooled to room temperature, neutralized to pH 8 with 1.0 N NaOH, and then evaporated to dryness under vacuum. The residue obtained in this manner was chromatographed on silica gel to give 941 mg of the desired product, HETR as a syrup.

EXAMPLE F

Preparation of 5-Deoxy-5-(monofluoroethylthio)ribose (MFETR)

1. MHETIR (2.0 g) was dissolved in 50 ml dry methylene chloride and cooled to −74° C. Diethylaminosulfur trifluoride (DAST) (3.0 ml) was injected under argon and after 2.5 hr, the reaction mixture was cautiously treated with saturated sodium bicarbonate solution. This was extracted with methylene chloride, the organic extract washed with saturated aqueous NaCl, dried over MgSO₄, filtered and evaporated under vacuum to give 1.89 g crude product. This was chromatographed on silica gel to give 677 mg methyl 5-deoxy-5-monofluoroethylthio-2,3-O-isopropylidene-riboside (MMFETIR).

2. MMFETIR (215 mg) in 0.1 N sulfuric acid (2875 μl) and dioxane (1400 μl) was heated at 80° C. for 2.75 hr. The solution was cooled to room temperature, neutralized with solid barium hydroxide, filtered and evaporated to dryness under vacuum. The 167 mg residue was chromatographed on Florisil to give 19 mg of the desired product, MFETR.

II Testing of the Compounds

EXAMPLE 1A—In Vitro Antitrypanosomal Activity of HETA and other Nucleosides.

The antitrypanosomal effects of HETA and other nucleosides were examined in the Lab 110 EATRO strain of *T. b. brucei* in culture.

Cells were cultured as described in Bacchi et al. Exp. Parasitol. 68, 392, 1989. Cells were then grown in the presence of the compounds for 3-5 days. Drugs were filtered, sterilized and added aseptically. Control cells achieved a maximum density of 1.5–3.5×10⁷/ml. Hemocytometer counts were made daily and the results were expressed as a percent of control growth. IC₅₀ plots were obtained by graphing log (drug) vs. percent growth inhibition.

As seen in Table 1A, which also shows the structures of the compounds tested, MFETA, CETA, BETA and HETA all exhibit significant activity in sharp contrast to closely related compounds ETA, PTA, MFPTA and HPTA. Also included in Table 1a are ETR and HETR, the ribose analogs of ETA and HETA. Both compounds were far less effective than HETA, indicating that trypanosomes do not utilize thioribose derivatives via MTA hydrolase and MTR kinase. Included in Table 1 are the IC₅₀ values for pentamidine and berenil, two agents which are in wide clinical use for the treatment of African trypanosomiasis. The activity of HETA is comparable to that of these currently used drugs.

TABLE 1

Trypanocidal Activity of MTA and MTR Analogs against *T. b. brucei* procyclic trypanosomes in T₂ medium.

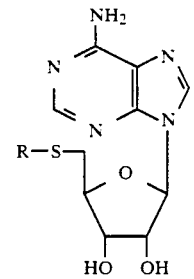

| COMPOUND | R | IC₅₀ (μM) |
|---|---|---|
| ETA | CH₃CH₂ | 138 |
| MFETA | FCH₂CH₂ | 5 |
| CETA | ClCH₂CH₂ | 2.5 |
| BETA | BrCH₂CH₂ | 0.5 |
| HETA | HOCH₂CH₂ | 0.5 |
| PTA | CH₃CH₂CH₂ | 46 |
| MFPTA | FCH₂CH₂CH₂ | 120 |
| HPTA | HOCH₂CH₂CH₂ | 170 |
| ETR* | | >100 |
| HETR* | | >100 |
| BERENIL* | | 0.2 |
| PENTAMIDINE* | | 0.2 |

*Structure not shown.

EXAMPLE 1B—Activity of HETA against bloodstream forms of African trypanosomes grown in vitro.

HETA was also evaluated against other bloodstream forms of African trypanosomes grown in vitro.

Cultures were initiated directly from infected mouse blood into Falcon 24 well plates containing 1 ml of Iscoves modified Dulbecco's medium plus 20% horse serum, 2 mM pyruvate, 2 mM glutamine, and 0.2 uM mercaptoethanol. Initial cell counts were $2.5-5.0 \times 10^5$/ml. Plates were incubated at 37 C in 5 percent $CO_2$. HETA was dissolved in the medium and filter sterilized. One half the volume of each well was replaced with fresh medium each day.

Cell counts were made daily. Data are given as percent inhibition of growth as determined by hemocytometer counts on day 4 as compared to control cultures without drug.

In Table 2, EATRO 110 is a strain of *T. b. brucei;* and KETRI 2002, and KETRI 243 are *T. b. rhodesiense* clinical isolates.

As seen in Table 2, HETA was found to have significant activity against the KETRI 2002 strain, a clinical isolate of *T. b. rhodesiense.*

TABLE 2

| um HETA | EATRO 100 | KETRI 2002 | KETRI 243 |
|---|---|---|---|
| 0.1 | 0 | 0 | 0 |
| 0.5 | 44 | 0 | 0 |
| 1.0 | 59 | 15 | 0 |
| 2.25 | 70 | 60 | 0 |

EXAMPLE 2—In Vivo Antitrypanosomal Activity of HETA

The in vivo activity of HETA was demonstrated using the LAB 110 EATRO mouse infection model.

As seen in Table 3, HETA not only gave high cure rates in these infected mice, but did so over a wide dose range, an indication of its minimal toxicity to the host.

TABLE 3

Susceptibility of *T. b. brucei* LAB 110 EATRO to HETA in vivo.

| Treatment[a] | Dose (mg/kg/day) | Time (Days) | MSD[b] | Number Cured Total | % Cured |
|---|---|---|---|---|---|
| None | — | — | 4.8[c] | 0/20 | 0 |
| Molecusol ® | [d] | 7 | 4.9 | 0/5 | 0 |
| MTA | 25 | 7 | 5.0 | 0/5 | 0 |
|  | 50 | 7 | 5.0 | 0/5 | 0 |
|  | 100 | 7 | 5.0 | 0/5 | 0 |
| HETA | 25 | 7 | 15.3 | 11/15 | 73 |
|  | 50 | 7 | 14.5 | 17/25 | 68 |
|  | 100 | 7 | 26.0 | 13/15 | 87 |
|  | 150 | 7 | 14.5 | 18/20 | 90 |
|  | 50 | 14 | 18.1 | 9/15 | 60 |
| MFETA | 10 | 7 | 5.0 | 0/5 | 0 |
|  | 25 | 7 | 11.6 | 2/5 | 40 |
|  | 50 | 7 | 10.6 | 0/5 | 0 |
|  | 100 | 7 | 12.0 | 2/5 | 40 |

[a] Animals were treated with surgically implanted miniosmotic pumps loaded as per manufacturers instructions with MTA, HETA or MFETA suspended in 10% Molecusol.
[b] Mean survival in days of animals dying of infection; this does not include cured animals.
[c] Range of survival of controls was 4-6 days.
[d] Pumps were loaded with 10% Molecusol only.

EXAMPLE 3—In Vitro Activity of HETA and other compounds against Isolates of *Trichomonas Vaginalis.*

Preliminary in vitro evaluation of HETA and other compounds against isolates of *Trichomonas vaginalis* was done. As seen in Table 4, HETA displays activity against the C1-NIH strain, and CETA was active against a metronidazole(Flagyl)-resistant strain, CDC-85.

Values are expressed as µg of compound per ml of medium required to inhibit growth and motility of the parasite in a multiwell plate assay as described by Meingassner, Mieth, Czok, Lindmark and Muller (1978) Antimicrob. Agents and Chemother. 13, 1-3. The present drug used for treatment metronidazole (Flagyl ®) is included for comparison. Strain ATCC 50143 (CDC-85) was refractory to chemotherapeutic dose levels of metronidazole. (ND = not done).

TABLE 4

Minimum lethal concentration (MLC) of compounds against *Trichomonas vaginalis* isolates.

| | ATCC 3001 | | ATCC 50143 | |
|---|---|---|---|---|
| Drug | 24 h | 48 hr | 24 h | 48 h |
| ETA | >187.5 | 187.5 | >187.5 | >187.5 |
| HETA | 46.9 | 11.7 | >187.5 | ND |
| MFETA | 93.7 | 23.4 | ND | ND |
| CETA | 93.7 | 23.4 | 187.5 | 11.7 |
| Flagyl | 6.25 | 0.78 | >800 | ND |

EXAMPLE 4—In Vitro Antimalarial Activity of HETA.

In studies undertaken against *P. Falciparum*, HETA was unexpectedly found to possess activity with an $IC_{50}$ value of approximately 22 µM. these data support the conclusion HETA has activity against a wide range of microorganisms.

The foregoing data indicate clearly that HETA has activity against a variety of parasitic protozoa. As noted, this agent inhibits an aspect of the metabolism of polyamines, i.e. the metabolism of MTA, whose potential for therapeutic intervention in parasitic organisms has been recognized but not previously exploited. Ghoda et al. [Molecular Biochem. Parasitol 27, 109 (1988] have previously demonstrated the presence in African trypanosomes of an MTA phosphorylase, as distinct from an MTA hydrolase. The apparent basis for the selectivity of HETA in the microorganism as opposed to mammalian cells, relates to a significant difference in the rate at which HETA is metabolized by mammalian and trypanosomal forms of the enzyme MTA phosphorylase. Whereas HETA has been found to be ineffectively metabolized by mammalian MTA phosphorylase, (HETA has a substrate activity of 34% relative to the MTA). HETA is metabolized by the *T. b. brucei* MTA phosphorylase as effectively as MTA itself as shown in Tables 5 and 6.

TABLE 5

Compounds as Substrates and/or Inhibitors of Mouse Liver MTA Phosphorylase

| | MTA Phosphorylase Activity[a] | |
|---|---|---|
| Compound | $K_1$ (µM) | Substrate (% Control) |
| MTA | 1.3 ($K_m$) | 100 |
| ETA | 1.9 | 95 |
| MFETA | 3.1 | 64 |
| CETA | 12 | 35 |
| BETA | 6.5 | 38 |
| HETA | 26 | 34 |
| PTA | 1.7 | 102 |
| MFPTA | 4.0 | 66 |

[a] MTA phosphorylase activity was assayed as described in Sufrin et al., J. Med. Chem., 32, 997 (1989).

TABLE 6

Activity of compounds as substrates for *T. b. brucei* MTA phosphorylase

| | Percent Control Activity[a] | |
|---|---|---|
| Substrate | +50 mM $PO_4$ | No $PO_4$ |
| MTA | 100 | 100 |
| ETA | 76.2 | 100 |
| BETA | 88.8 | 120 |
| MFETA | 75.3 | 109.1 |
| CETA | 60 | 94.4 |

TABLE 6-continued

Activity of compounds as substrates for *T. b. brucei* MTA phosphorylase

| Substrate | Percent Control Activity[a] | |
|---|---|---|
| | +50 mM PO$_4$ | No PO$_4$ |
| HETA | 85 | 100 |
| PTA | 57.5 | 96.4 |
| MFPTA | 47.5 | 116.4 |
| HPTA | 72.5 | 101.8 |

[a]MTA phosphorylase was assayed according to Ghoda et al., using 200 μM MTA (saturating) or analogs as substrates. Specific activities of the dialyzed enzyme preparations were with 50 mM PO$_4$, 104.97 n moles/mg protein/h; without PO$_4$, 28.27 n moles/mg protein/h. Results are expressed as percent activity compared to as substrate with and without PO$_4$, respectively.

Example 5—Therapeutic Evaluation of Compounds

L1210, L5178Y and MOLT-4 cells lines were grown in RPMI 1640 and 10% Nu Serum (Collaborative Research Inc., Lexington, MA) and CCRF-CEM cells were grown in 10% Horse Serum (Gibco Laboratories, Grand Island, NY) and maintained as previously described for suspension cultures by Pera et al. in Cancer Res. 46, 1148, 1986. Cell cultures (0.3×10$^5$ cells/ml) were treated with each compound at 0.1 to 1000 μM to determine the concentration that inhibited growth by 50% (IC$_{50}$) at 48 hr for the L1210 and L5178Y cells and at 96 hr for the CCRF-CEM and MOLT-4 cells. The incubation times allowed approximately 4 cell doublings in each cell line. All compounds were freshly prepared prior to treatment by dissolving in DMSO and diluting in serum-free media. Cells were counted by electron particle counting (Model XF′ Coulter Counter; Coulter Electronics, Hialeah, FL.). The data and results are shown in Table 7.

For each compound, the concentrations required to inhibit cell growth by 50% (IC$_{50}$ values) are shown in Table 7 for two murine leukemic cell lines, L1210 and L5178Y [MTA phosphorylase-deficient and MTA phosphorylase-containing, respectively] and two human leukemic cell lines, CCRF-CEM and MOLT-4 [MTA phosphorylase-deficient and MTA phosphorylase-containing, respectively]. ETA, MFETA, HETA and PTA had lower IC$_{50}$ values in the L5178Y cells than in the L1210 cells. MFETA was the most potent analog and demonstrated the most significant difference in IC$_{50}$ values between the two lines. This differential is consistent with the possibility that, in L5178Y cells, MFETA is cleaved by MTA phosphorylase to the growth inhibitory metabolite, 5-monofluoroethylthioribose-1-phosphate (MFETR-1-P).

The compounds of the invention were more potently growth inhibitory in the human CCRF-CEM and MOLT-4 cells and displayed a consistent differential between these cell lines in their IC$_{50}$ values. MFETA was the most growth inhibitory compound in all four cell lines tested.

TABLE 7

Effects of MTA, ETA, PTA and 5′-Haloalkyl Compounds on Growth of Paired (MTA Phosphorylase-containing and MTA Phosphorylase-deficient) Human and Murine Tumor Cell Lines

| Cell Line | Mouse | | Human | |
|---|---|---|---|---|
| | L1210 | L5178Y | CCRF-CEM | MOLT-4 |
| Enzyme[1] Activity | <20 | 2253 | <20 | 2230 |
| Analog | IC$_{50}$ (μM) | | | |
| | 48 h | | 96 h | |
| MTA | 850 ± 120 | 200 ± 45 | 150 ± 60 | 11 ± 7 |
| ETA | 800 ± 100 | 250 ± 100 | 200 ± 100 | 20 ± 10 |
| MFETA | 150 ± 50 | 60 ± 35 | 75 ± 20 | 10 ± 3 |
| CETA | 250 | 200 | 240 ± 90 | 30 ± 20 |
| BETA | 150 | 150 | 250 ± 50 | 25 ± 10 |
| HETA | 1000 | 500 | 100 | 40 |
| PTA | 1000 | 500 | 160 | 45 |
| MFPTA | 600 | 600 | 160 | 25 |

[1]Intracellular MTA phosphorylase activity expressed in pmol/min/mg protein.

Example 6—In Vivo Therapeutic Evaluation of MFETA

The antitumor effects of MFETA were evaluated in DBA/2N mice (Charles River) who received i.p. transplants of 10$^6$ L1210 leukemic cells or 10$^6$ L5178Y leukemic cells on day 0 according to protocols described previously by Bernacki et al., Cancer Res. 47, 799, 1987. The increase in life span (% ILS) of treated animals relative to untreated, tumor-bearing animals was used as the measure of their therapeutic effectiveness at specified dose regimens. The data and results are shown in Table 8.

The results of the in vivo studies agree with cell culture data.

TABLE 8

Comparative Antitumor Effects of MFETA in L1210 Leukemic Mice and L5178Y Leukemic Mice

| Tumor | Number of Treated Animals | Dosage[a] (mg/kg) | Survival Parameters | | | | | |
|---|---|---|---|---|---|---|---|---|
| | | | Mean Death Weight (g) | Range (days) | Median (days) | Mean ± SD (days) | % ILS[b] | P |
| L1201 | 13 | untreated | 22.0 | 6–8 | 7 | 7.1 ± 0.2 | 0 | — |
| | 5 | 10 | 23.7 | 6–8 | 8 | 7.2 ± 0.5 | 14 | 0.37 |
| | 5 | 50 | 24.5 | 7–8 | 8 | 7.8 ± 0.2 | 14 | 0.18 |
| | 10 | 100 | 22.8 | 7–9 | 8 | 7.9 ± 0.2 | 14 | 0.08 |
| | 5 | 200 | 18.4 | 6–11 | 9 | 8.8 ± 0.8 | 28 | 0.01 |
| | 5 | 300 | 18.8 | 2–3 | 2 | 2.2 ± 0.2 | −72 | NS |
| L5178Y | 13 | untreated | 21.7 | 7–10 | 8 | 8.5 ± 0.2 | 0 | — |
| | 5 | 10 | 19.7 | 8–10 | 9 | 9.0 ± 3 | 12 | 0.22 |
| | 5 | 50 | 21.6 | 8–11 | 11 | 10.0 ± 6 | 37 | 0.03 |
| | 10 | 100 | 23.1 | 8–12 | 11 | 10.5 ± 4 | 37 | <0.01 |
| | 5 | 200 | 20.4 | 9–14 | 13 | 12.4 ± 9 | 62 | <0.01 |
| | 5 | 300 | 18.4 | 2–4 | 2 | 2.6 ± 4 | −75 | NS |

[a]MFETA was administered i.p. on days 1, 2, 3, 4, 5 following i.p. implantation of 10$^6$ tumor cells on day 0.
[b]% ILS is the percentage of increase in life span.

What is claimed is:

1. A compound selected from the group consisting of 5′-deoxy-5′-(monofluoroethylthio)adenosine (MFETA); 5′-deoxy-5′-(chloroethylthio)adenosine (CETA) and 5′-deoxy-5,-(bromoethylthio)adenosine (BETA).

2. The compound 5′-deoxy-5′-(monofluoroethylthio)adenosine (MFETA).

3. The compound 5'-deoxy-5'-(chloroethylthio)adenosine (CETA).

4. The compound 5'-deoxy-5'-(bromoethylthio)adenosine (BETA).

5. A method for treating infections caused by 5'-deoxy-5'-methylthioadenosine (MTA) phosphorylase-containing pathogenic microorganisms which comprises administering a nontoxic, effective amount of an adenosine compound to a human being or an animal in need of such a treatment, wherein said adenosine compound is selected from one or more of the following compounds:

5'-deoxy-5'-(hydroxyethylthio)adenosine (HETA);
5'-deoxy-5'-(monofluoroethylthio)adenosine (MFETA);
5'-deoxy-5'-(chloroethylthio)adenosine (CETA); and
5'-deoxy-5'-(bromoethylthio)adenosine (BETA).

6. A method for treating infections caused by 5'-deoxy-5'-methylthioadenosine (MTA) phosphorylase-containing pathogenic microorganisms which comprises administering a nontoxic, effective amount of 5'-deoxy-5'-(hydroxyethylthio)adenosine to a human being or an animal in need of such a treatment.

7. The method of claim 5 wherein the microorganism is selected from:

*Trypanosoma brucei brucei,*
*Trypanosoma brucei rhodesiense,*
*Trypanosoma brucei gambiense,*
*Trypanosoma cruzi,*
*Trichomonas vaginalis,*
*Plasmodium falciparum,*
*Leishmania donovani,*
*Leishmania tropica,* and
*Leishmania brasiliensis.*

8. A method for treating infections caused by *Trypanosoma brucei brucei, Trypanosoma brucei rhodesiense* or *Trypanosoma brucei gambiense,* which comprises administering a nontoxic, effective amount of an adenosine compound to a human being or an animal in need of such a treatment, wherein said adenosine compound is selected from one or more of the following compounds:

5'-deoxy-5'-(hydroxyethylthio)adenosine (HETA);
5'-deoxy-5'-(monofluoroethylthio)adenosine (MFETA);
5'-deoxy-5'-(chloroethylthio)adenosine (CETA); and
5'-deoxy-5'-(bromoethylthio)adenosine (BETA).

9. A method for treating infections caused by *Trypanosoma brucei brucei, Trypanosoma brucei rhodesiense* and *Trypanosoma brucei gambiense,* which comprises administering a nontoxic, effective amount of 5'-deoxy-5'-(hydroxyethylthio)adenosine to a human being or an animal in need of such a treatment.

* * * * *